United States Patent

Ray et al.

[11] Patent Number: 5,567,817
[45] Date of Patent: Oct. 22, 1996

[54] TRIAZOLE ANTIFUNGAL AGENTS

[75] Inventors: Stephen J. Ray, Deal; Kenneth Richardson, Birchington; both of England

[73] Assignee: Pfizer Inc., New York, N.Y.

[21] Appl. No.: 432,414

[22] Filed: May 1, 1995

Related U.S. Application Data

[60] Continuation of Ser. No. 139,972, Oct. 20, 1993, abandoned, which is a division of Ser. No. 956,569, Oct. 5, 1992, Pat. No. 5,278,175, which is a continuation of Ser. No. 646,564, Jan. 25, 1991, abandoned.

[30] Foreign Application Priority Data

Feb. 2, 1990 [GB] United Kingdom .................. 9002375

[51] Int. Cl.$^6$ ............................................. C07D 403/10
[52] U.S. Cl. ........................................................ 544/333
[58] Field of Search ............................. 544/333; 514/256

[56] References Cited

U.S. PATENT DOCUMENTS 4,952,232  8/1990  Cuomo et al. ............................ 71/92
5,116,844  5/1992  Dickinson et al. .................... 514/269

FOREIGN PATENT DOCUMENTS 332387  9/1989  European Pat. Off. .
3813841  12/1988  Germany .......................... 548/266.6

Primary Examiner—Patricia L. Morris
Attorney, Agent, or Firm—Peter C. Richardson; Paul H. Ginsburg; Bryan C. Zielinski

[57] ABSTRACT

The invention provides antifungal compounds of the formula:

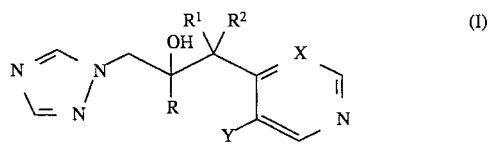

and pharmaceutical salts thereof,
wherein
R is phenyl substituted by 1 to 3 substituents each independently selected from halo, —$CF_3$ and —$OCF_3$;
$R^1$ is $C_1$–$C_4$ alkyl;
$R^2$ is H or $C_1$–$C_4$ alkyl;
X is CH or N; and
Y is F or Cl.

12 Claims, No Drawings

TRIAZOLE ANTIFUNGAL AGENTS

This is a continuation of U.S. application Ser. No 08/139,972, filed Oct. 20, 1993, now abandoned, which is a divisional of U.S. application Ser. No. 07/956,569, filed on Oct. 5, 1992, issued as U.S. Pat No. 5,278,175, which is a continuation of U.S. application Ser. No. 07/646,564, filed on Jan. 25, 1991, now abandoned.

BACKGROUND OF THE INVENTION

This invention relates to triazole derivatives which have antifungal activity.

More particularly this invention relates to 2-aryl-3-(3-halopyridin-4-yl or 5-halopyridin-4-yl)-1-(1H-1,2,4-triazol-1-yl)alkan2-ol derivatives which are useful in the treatment of fungal infections in animals, including human beings.

Some of the compounds of the present invention are disclosed in a general sense in our European Patent Application No. 89307920.2(EP-A-0357241) but none of these are specifically described or exemplified therein.

SUMMARY OF THE INVENTION

It has now been discovered that the compounds of the present invention have a surprisingly high level of antifungal activity, in particular against *Aspergillus spp.* fungi, which is mainly attributable to their unexpectedly good pharmacokinetic properties which result in longer half-lives (t½ values). The invention provides antifungal agents of the formula:

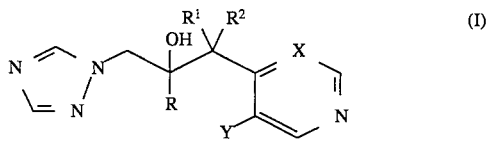

and pharmaceutically acceptable salts thereof,
wherein
R is phenyl substituted by 1 to 3 substituents each independently selected from halo, —$CF_3$ and —$OCF_3$;
$R^1$ is $C_1$–$C_4$ alkyl;
$R^2$ is H or $C_1$–$C_4$ alkyl;
X is CH or N; and
Y is F or Cl.

In the above definition of compounds of the formula (I) halo is F, Cl, Br or I and $C_3$ and $C_4$ alkyl groups may be straight- or branched-chain. Preferred alkyl groups are methyl and ethyl.

Examples of R include 2-fluorophenyl, 4-fluorophenyl, 2-chlorophenyl, 4-chlorophenyl, 2-bromophenyl, 2-iodophenyl, 2-trifluoromethylphenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, 4-bromo-2,5-difluorophenyl and 2-trifluoromethoxyphhenyl.

R is preferably phenyl substituted by 1 to 3 halo substituents, more preferably by 1 or 2 halo substituents.

Yet more preferably R is phenyl substituted by 1 or 2 substituents each independently selected from fluoro and chloro.

Preferred individual embodiments of R include 2-fluorophenyl, 4-fluorophenyl, 2,4-difluorophenyl, 2-chlorophenyl and 2,4-dichlorophenyl.

Most preferably R is 2-fluorophenyl, 2,4-difluorophenyl, 2-chlorophenyl or 2,4-dichlorophenyl.

Preferably $R^1$ is methyl.

Preferably $R^2$ is H or methyl.
Most preferably $R^2$ is H.
Preferably $R^1$ is methyl and $R^2$ is H or methyl.
Most preferably $R^1$ is methyl and $R^2$ is H.
Preferably X is N.
Preferably Y is F.

The pharmaceutically acceptable salts of the compounds of the formula (I) include acid addition salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts. For a review on suitable pharmaceutical salts see Berge et al, J. Pharm. Sci., 66, 1–19 (1977).

Where $R^1$ is identical to $R^2$, the compounds of the formula (I) contain one chiral centre and therefore exist as a pair of enantiomers (a racemate).

Where $R^1$ and $R^2$ are different, the compounds of the formula (I) contain at least two chiral centres (*) and therefore exist as at least two diastereoisomeric pairs of enentiomers, i.e.

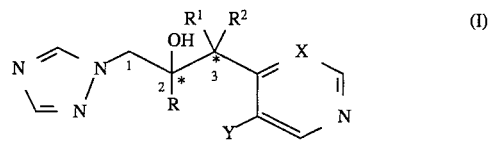

The invention includes both the individual stereoisomers of the compounds of the formula (I) together with mixtures thereof. Separation of diastereisomers may be achieved by conventional techniques, e.g. by fractional crystallisation, chromatography or H.P.L.C. of a diastereoisomeric mixture of a compound of the formula (I) or a suitable salt or derivative thereof. An individual enantiomer of a compound of the formula (I) may also be prepared from a corresponding optically pure intermediate or by resolution, either by H.P.L.C. of the racemate using a suitable chiral support or by fractional crystallisation of the diastereoisomeric salts formed by reaction of the racemate with a suitable optically active acid, e.g. 1R-(–)- or 1S-(+)-10-camphorsulphonic acid.

The preferred compounds of the formula (I) when $R^2$ is H have the 2R,3S- configuration, i.e.

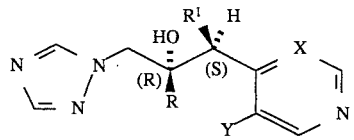

Particularly preferred individual embodiments of compounds of the present invention are
2R,3S-2-(2,4-difluorophenyl)-3-(3-fluoropyridin-4-yl)-1-(1H- 1,2,4-triazol-1-yl)butan-2-ol,
2R,3S-2-(2-chlorophenyl)-3-(3-fluoropyridin-4-yl)-1-(1H-1,2,4-triazol-1-yl)butan-2-ol,
2R,3S-2-(2-fluorophenyl)-3-(3-fluoropyridin-4-yl)-1-(1H-1,2,4-triazol-1-yl)butan-2-ol,
2R,3S-2-(2,4-difluorophenyl)-3-(5-fluoropyrimidin-4-yl)-1-(1H-1,2,4-triazol- 1-yl)butan-2-ol, and 2R,3S-2-(2,4-dichlorophenyl)-3- (5-fluoropyrimidin-4yl)-1-(1H-1,2,4-triazol-1-yl)butan-2-ol, and pharmaceutically acceptable salts thereof.

DETAILED DESCRIPTION OF THE INVENTION

The compounds of the formula (I) provided by the invention may be prepared by the following methods:

1) All the compounds of the formula (I) may be prepared as shown in Scheme 1:

Scheme 1

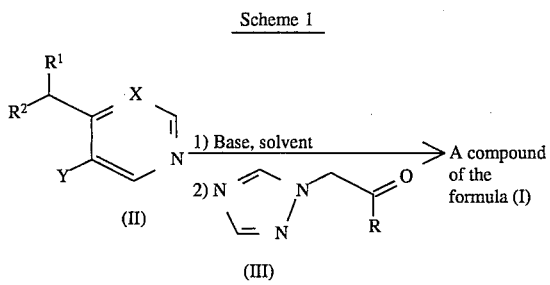

wherein R, $R^1$, $R^2$, X and Y are as defined for a compound of the formula (I).

In a typical procedure a compound of the formula (II) is deprotonated by the addition of approximately on equivalent of a suitable base, e.g. lithium diisopropylamide, or sodium or potassium bis(trimethylsilyl)amide, and the resulting salt (preferably the lithium, sodium or potassium salt) is reacted in situ with a ketone of the formula (III). The reaction is typically carried out at from −80° to −50° C., preferably at from −70° to −60° C., in a suitable organic solvent, e.g. tetrahydrofuran, toluene or diethyl ether, and under an inert atmosphere, e.g. nitrogen or argon.

The starting materials of the formula (II) are either known compounds (e.g. see D. L. Comins et al, Heterocycles, 22, 339 (1984)) or may be prepared by conventional procedures in accordance with literature precedents. The staring materials of the formula (III) are either known compounds (e.g. see EP-A-44605, EP-A-69442 or GB-A-1464224) or may be prepared by similar methods to those described therefor.

2) All the compounds of the formula (I) may also be prepared as shown in Scheme 2:

Scheme 2

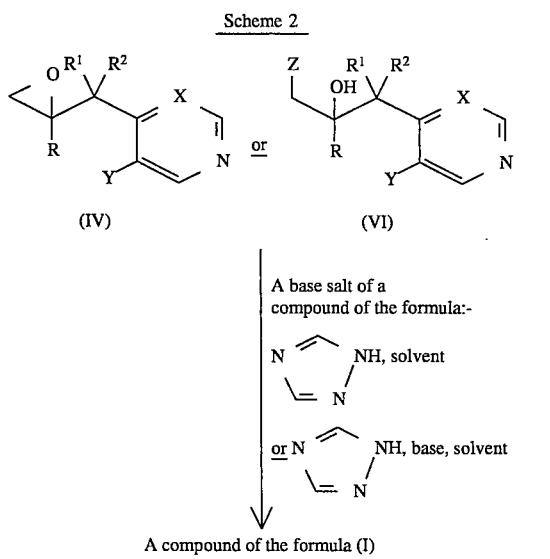

wherein R, $R^1$, $R^2$, X and Y are as defined for a compound of the formula (I) and Z is a suitable leaving group, e.g. chloro, bromo or $C_1$-$C_4$alkanesulphonyloxy (such as methanesulphonyloxy). Examples of suitable base salts of 1H-1,2,4-triazole are alkali metal, preferably sodium and potassium, and tetraalkylammonium, preferably tetra-n-butylammonium (see U.S. Pat. No. 4,259,505), salts.

The reaction is preferably carried out using an epoxide of the formula (IV) as the starting material. If a compound of the formula (IV) is used in this process, it is probable that the reaction mechanism dictates, at least in part, that the corresponding epoxide of the formula (IV) is formed in situ under the reaction conditions. The process is therefore, in this respect, similar to that utilising an epoxide of the formula (IV) as the starting material.

When a base salt of 1H-1,2,4-triazole is used, the reaction is typically carried out at from room temperature to 100° C., preferably at about 60° C. when using the sodium salt of 1H-1,2,4-triazole, and preferably at abour room temperature when using the corresponding tetra-n-butylammonium salt, in a suitable organic solvent, e.g. N,N-dimethylformamide or tetrahydrofuran.

Alternatively, the reaction may be carried ort using 1H-1, 2,4-triazole in the presence of an additional suitable base, e.g. $Na_2CO_3$ or $K_2CO_3$, preferably at from 50° to 100° C. in a suitable solvent, e.g. N,N-dimethylformamide, methanol or aqueous acetone.

The intermediates of the formula (IV) and (VI) may be prepared by conventional techniques as summarised by the following methods shown in Schemes 3 and 4:

Scheme 3

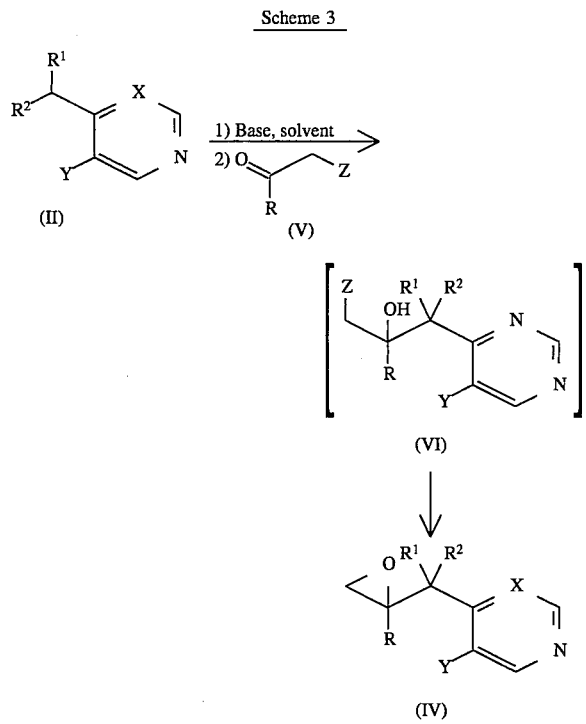

wherein R, $R^1$, $R^2$, X and Y are as defined for a compound of the formula (I) and Z is a leaving group, preferably Cl or Br.

In a typical procedure, a compound of the formula (II) is deprotonated by the addition of approximately one equivalent of a suitable base, e.g. lithium diisopropylamide, or sodium or potassium bis(trimethylsilyl)amide, and the resulting organometallic intermediate is reacted in situ with a compound of the formula (V). The reaction is typically carried out at from −80° to −50° C., preferably at about −70° C., in a suitable organic solvent, e.g. tetrahydrofuran, toluene or diethyl ether, and under an inert atmosphere, e.g. nitrogen or argon. The compound of the formula (VI) formed need not be isolated and is generally cyclised in situ after a period of stirring at a higher temperature, e.g. room temperature, to provide an oxirane of the formula (IV).

A compound of the formula (IV) when Z is chloro or bromo may also be prepared by reacting an epoxide if the formula (IV) with the appropriate hydrogen halide under anhydrous conditions.

Alternatively, a compound of the formula (IX) or (X) may be prepared by reacting, respectively, a compound of the formula (VIII) or (IX) with approximately one equivalent of a suitable base, e.g. sodium hydride, followed by alkylation of the resultant carbanion in situ with a suitable alkylation agent. The reaction is typically carried out at from 0° C. to room temperature in a suitable organic solvent, e.g. N,N-dimethylfromamide.

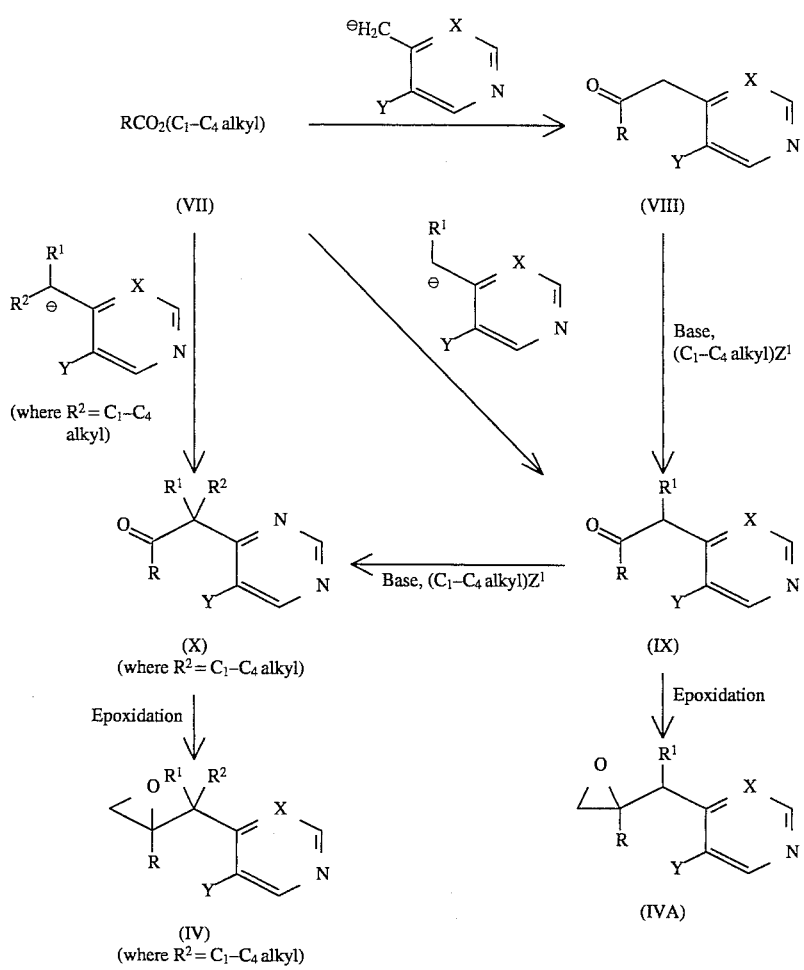

wherein R, $R^1$, $R^2$, X and Y are defined for a compound of the formula (I) and $Z^1$ is a suitable leaving group, e.g. Cl, Br, I or methanesulphonyloxy.

In a typical procedure a compound of the formula (VIII), (IX) or (X) is prepared directly from an ester of the formula (VII) by reaction with an organometallic intermediate derived by deprotonation of a compound of the formula:

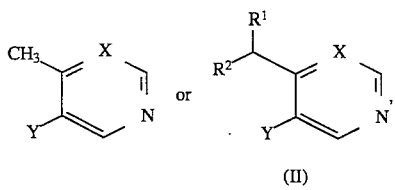

as appropriate, wherein $R^1$, $R^2$, X and Y are as defined for a compound of the formula (I), with approximately on equivalent of a suitable base, e.g. lithium diisopropylamide or sodium bis(trimethylsilyl)amide. The reaction is typically carried out at from –80° to –50° C., preferably at about –70° C., in a suitable organic solvent, e.g. tetrahydrofuran or diethyl ether, and under an inert atmosphere, e.g. nitrogen or argon.

Preferably, alkylation of a compound of the formula (VIII) or (IX) is performed under phase transfer conditions, e.g. using NaOH/[CH$_3$(CH$_2$)$_3$]$_4$N $\oplus$ $\ominus$HSO$_4$/H$_2$O/CHCl$_3$/ (C$_1$–C$_4$alkyl)Z$^1$ (wherein Z$^1$ is preferably iodo), at from 0° to room temperature, and typically at room temperature.

Epoxidation of a ketone of the formula (IX) or (X) is performed using conventional methods, e.g. using dimethyloxosulphonium methylide (e.g. see J.A.C.S. [1965], 87, 1353) or chloromethyllithium (e.g. see Tet. Lett. [1986], 795).

3) The compounds of the formula (I) wherein R, $R^1$, $R^2$ and Y are as defined for a compound of the formula (I) and X is N may be prepared as shown in Scheme 5:

Scheme 5

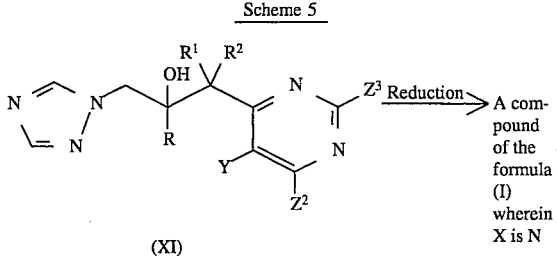

wherein R, $R^1$, $R^2$ and Y are as defined for a compound of the formula (I) and $Z^2$ and $Z^3$ are each independently selected from H and a group that may be selectively removed by reduction, with the proviso that $Z^2$ and $Z^3$ cannot both be H. Preferably $Z^2$ is the group that may be selectively removed by reduction and $Z^3$ is H. Preferably the group that may be selectively removed by reduction is halo (defined as F, Cl, Br or I) and most preferably is chloro.

When said group is halo, preferably chloro, the preferred method of reduction is by hydrogenolysis. In a typical procedure a compound of the formula (XI) is subjected to hydrogenolysis using a suitable catalyst, e.g. palladium-on-charcoal, and a suitable solvent, e.g. ethanol, optionally in the presence of an additional suitable solvent, e.g. ethanol, optionally in the presence of an additional suitable base, e.g. sodium acetate. The reaction may be carried out at from room temperature to the reflux temperature of the solvent and at a pressure of from 1 to 5 atmospheres (100 kPa to 500 kPa), but generally proceeds satisfactorily at about room temperature and at about atmospheric pressure.

The intermediates of the formula (XI) wherein one of $Z^2$ and $Z^3$ is H and the other is a group that may be selectively removed by reduction may be conveniently prepared as shown in Scheme 6:

Scheme 6

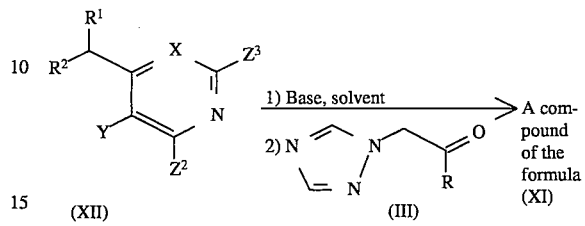

wherein R, $R^1$, $R^2$ and Y are as defined for a compound of the formula (I) and one of $Z^2$ and $Z^3$ is H and the other is a group that may be selectively removed by reduction. The reaction may be carried out by the similar procedure to that described in Method (1).

The intermediates of the formula (XI) wherein one of $Z^2$ and $Z^3$ is H and other is a group that may be selectively removed by reduction may also be prepared by an analogous procedure to that described in Method (2).

The starting materials of the formula (XII) May be prepared by conventional procedures such as are illustrated in the following Preparations section.

The intermediates of the formula (XI) wherein $Z^2$ and $Z^3$ are each a group that may be selectively removed by reduction may be prepared by an analogous procedure to that described in Method (2) by using an appropriate epoxide starting material which may be prepared as shown in Scheme 7 using conventional procedures:

Scheme 7

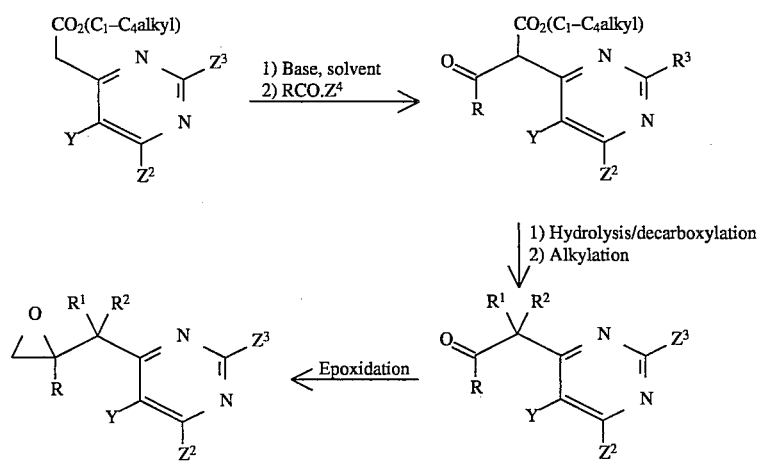

wherein R, $R^1$, $R^2$ and Y are as defined for a compound of the formula (I), $Z^2$ and $Z^3$ are each a group that may be selectively removed by reduction and $Z^4$ is chloro or $C_1$-$C_4$ alkoxy.

All of the above reactions are conventional and appropriate reagents and reaction conditions for their performance and procedures for isolating the desired products will be well known to those skilled in the art, in accordance with literature precedents and by reference to the Examples hereto.

A pharmaceutically acceptable acid addition salt is readily prepared by mixing together solutions containing the free base and the desired acid. The salt generally precipitates from solution and is collected by filtration, or is recovered by evaporation of the solvent.

The compounds of the formula (I) and their salts are antifungal agents, useful in the curative or prophylactic treatment of fungal infections in animals, including humans. For example, they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, species of Candida (e.g. *Candida albicans*), *Cryptococcus neoformans, Aspergillus flavus, Aspergillus fumigatus*, Coccidioides, Paracoccidioides, Histoplasma or Blastomyces.

The compounds of the present invention have been found to have unexpectedly good activity against the clinically important *Aspergillus spp.* fungi. This is mainly attributable to their unexpectedly good pharmacokinetic properties which result in longer half-lives (t½ values).

The in vitro evaluation of the antifungal activity of the compounds can be performed by determining the minimum inhibitory concentration (m.i.c.), which is the concentration of the test compounds, in a suitable medium, at which growth of the particular micro-organism fails to occur. In practice, a series of agar plates, each having the test compound incorporated at a particular concentration, is inoculated with a standard culture of, for example, *Candida albicans*, and each plate is then incubated for 48 hours at 37° C. The plates are them examined for the presence or absence of growth of the fungus and the appropriate m.i.c. value is noted. Other micro-organisms used in such tests can include *Aspergillus fumigatus, Trichophyton spp., Microsporum spp., Epidermophyton floccosum, Coccidioides immitis* and *Torulopsis glabrata*.

The in vivo evaluation of the compounds can be carried out at a series of dose levels by intraperitoneal or intravenous injection, or by oral administration, to mice which are inoculated with, e.g., a strain of *Candida albicans* or *Aspergillus fumigatus*. Activity is based on the survival of the treated group of mice after the death of an untreated group of mice. The dose level at which the compound provides 50% protection against the lethal effect of the infection ($PD_{50}$) is noted. For *Aspergillus spp.* infection models, the number of mice cured of the infection after a set dose allows further assessment of activity.

For human use, the antifungal compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring and colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The solubility of a compound of the formula (I) in an aqueous medium may be improved by complexation with a hydroxyalkyl derivative of a cyclodextrin in the preparation of an appropriate pharmaceutical composition. Preferably the cyclodextrin used is alpha-, beta-, or gamma-cyclodextrin and most preferably is beta-cyclodextrin. Preferably the hydroxyalkyl derivative is a hydroxypropyl derivative.

For oral and parenteral administration to human patients, the daily dosage level of the antifungal compounds of the formula (I) and their salts will be from 0.01 to 20 mg/kg (in single or divided doses) when administered by either the oral or parenteral route. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository of pessary, or they may be applied topically in the form of a lotion, solution, cream, ointment, or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

Thus the invention further provides a pharmaceutical composition comprising a compound of the formula (I), or a pharmaceutically acceptable salt thereof, together with a pharmaceutically acceptable diluent or carrier.

The invention yet further provides a compound of the formula (I), or a pharmaceutically acceptable salt or composition thereof, for use as a medicament, in a particular as an antifungal agent.

The invention also provides the use of a compound of the formula (I), or of a pharmaceutically acceptable salt or composition thereof, for the manufacture of an antifungal agent.

The invention yet further provides a method of treating an animal (including a human being) to cure or prevent a fungal infection, which comprises treating said animal with an effective amount of a compound of the formula (I), or with, as appropriate, a pharmaceutically acceptable salt or composition thereof.

The invention also provides novel intermediates of the formulae (IV), (VI) and (XI), 4-ethyl-5-fluoropyridimine and 4-chloro-6-ethyl-5-fluoropyrimidine.

The following Examples illustrate the preparation of the compounds of the formula (I). It is believed that enantiomeric pair B, when referred to in any following Example of Preparation, and the products of Examples 1, 3, 4 and 5 (in each of which only one of the two possible enantiomeric pairs was obtained) are a racemic mixture of the 2R,3S- and 2S,3R- enantiomers.

11
EXAMPLE 1

3-(3-Chloropyridin-4-yl)-2-(2,4-difluorophenyl)-
1-(1H-1,2,4-triazol- 1-yl)butan-2-ol

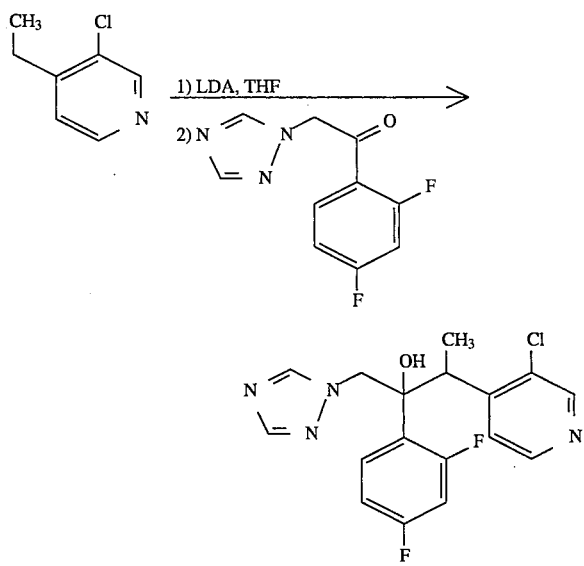

To a solution of diisopropylamine (1.01 g, 10 mmol) in dry THF (60 ml) at −60° C. and under a nitrogen atmosphere was added dropwise a 1.6M solution of n-butyllithium in hexane (6.25 ml, 10 mmol). The mixture was allowed to warm to −20° C. them recooled to −70° C. and to the resulting solution of lithium diisopropylamide (LDA) (10 mmol) at −70° C. was added dropwise 3-chloro-4ethylpyridine (see D. L. Comins et al, Heterocycles, 22, 339 (1984)) (1.41 g, 10 mmol). The resulting mixture was stirred at this temperature for 15 minutes after which time a solution of 1-(2,4-difluorophenyl)-2-(1H-1,2,4-triazol-1-yl)ethanone (2.23 g, 10 mmol) in THF (15 ml) was added. This mixture was allowed to warm to room temperature over a 30 minute period and the reaction was quenched by the addition of water (30 ml) and extracted with ethyl acetate (3×60 ml). The combined organic extracts were dried over magnesium sulphate, filtered, concentrated under reduced pressure and the title compound isolated by "flash " chromatography on silica eluting with ethyl acetate. The product was recrystallised from ethyl acetate (yield=0.46 g), m.p. 182°–184° C. Found: C,55.76; H,4.15; N,15.23; $C_{17}H_{15}ClF_2N_4O$ requires: C,55.98; H,4.14; N,15.36%.

EXAMPLE 2

2-(2,4-Difluorophenyl)-3-(3-fluoropyridin-4-yl)-
1-(1H-1,2,4-triazol- 1-yl)butan-2ol

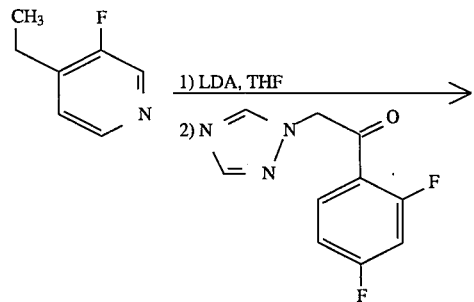

12
-continued

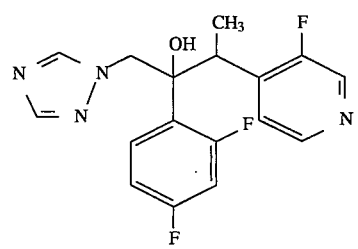

The reaction was carried out by a similar method to that described for Example 1 using 4-ethyl-3-fluoropyridine (see Preparation 1) instead of 3-chloro-4-ethylpyridine as the starting material. Column chromatography of the crude reaction product on silica using ethyl acetate as the eluant first gave, after combination and evaporation of the appropriate fractions, the title compound, enantiomeric pair A, m.p. 178°–181° C., which was characterised by $^1$H-NMR spectroscopy.

$^1$H-NMR (CDCl$_3$): δ=1.6 (d, 3H), 3.95 (q, 1H), 4.7 and 5.15 (AB q, 2H), 5.1 (s, 1H (OH)), 6.5 (m, 1H), 6.7 (m, 1H), 6.95 (m, 1H), 7.45 (t, 1H), 7.8 (s, 1H), 7.95 (s, 1H), 8.15 (s, 1H), 8.25 (d, 1H) ppm.

Further elution with 95:5 ethyl acetate/methanol provided, after combination and evaporation of the appropriate fractions, the impure title compound, enantiomeric pair B. This was further purified by column chromatography on silica using 93:7:1 dichloromethane/methanol/0.880 aqueous ammonia as the eluant. The appropriate fractions were combined and evaporated to provide, after trituration with diethyl ether, the title compound, enantiomeric pair B, m.p. 188°–9° C. Found: C,57.63; H,4.32; N,15.71; $C_{17}H_{15}F_3N_4O.0.25$ $H_2O$ requires: C,57.87; H,4.43; N,15.88%.

Enantiomeric pair B was resolved by H.P.L.C. using a chiral support (CHIRACEL ® OG) and eluting with 1:1 isopropanol/hexane. The appropriate fractions were combined and evaporated to provide the resolved individual enantiomers, each contaminated with the chiral support.

Each impure enantiomer was further purified by column chromatography on silica using dichloromethane/methanol (95:5) as the eluant. The appropriate fractions were combined and evaporated to give, after trituration with hexane/diethyl ether, a purified individual enantiomer.

One enantiomer of m.p. 57°–59° C. and $[\alpha]_D^{25}$ −59° (c=1 mg/ml in methanol) and another of m.p. 56°–57° C. and $[\alpha]_D^{25}$ +57° (c=1 mg/ml in methanol) were obtained.

EXAMPLES 3 to 6

The following tabulated compounds of the general formula:

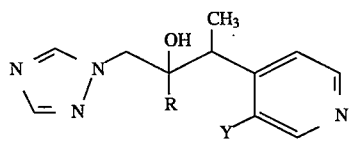

were prepared by a similar method to that described for Example 1 using the appropriate 4-ethyl-3-halopyridine and 1-(halophenyl)-2-(1H-1,2,4-triazol- 1-yl)ethanone as the starting materials.

| Example No. | R | 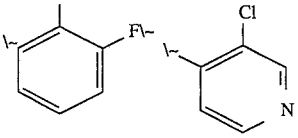 | m.p (°C.) | Analysis |
|---|---|---|---|---|
| 3[(1)(7)] | [2-fluorophenyl] | Cl (2)\~ | 166–167 | Found: C,58.92; H,4.85; N,15.99; $C_{17}H_{16}ClFN_4O$ requires: C,58.88; H,4.65; N,16.16% |
| 4[(1)(7)] | [2-chlorophenyl] | F (3)\~ | 153–155 | Found: C,59.05; H,4.84; N,16.06; $C_{17}H_{16}ClFN_4O$ requires: C,58.88; H,4.65; N,16.16%. |
| 5[(4)(5)] | [2-fluorophenyl] | Cl (2)\~ | 156–157 | Found: C,61.45; H,4.96; N,16.85; $C_{17}H_{16}F_2N_4O$ requires: C,61.81; H,4.88; N,16.96% |
| 6[(6)] | [4-fluorophenyl] | Cl (2)\~ | Enantiomeric pair A:- 112–114<br>Enantiomeric pair B:- 184–185 | Found: C,56.06; H,4.94; N,15.42; $C_{17}H_{16}ClFN_4O.H_2O$ requires: C,55.97; H,4.97; N,15.36%.<br>Found: C,59.17; H,4.63; N,16.15; $C_{17}H_{16}ClFN_4O$ requires: C,58.88; H,4.65; N,16.16%. |

(1) Column chromatography was carried out on silica with a gradient elution using 2:1 ethyl acetate/dichloromethane followed by ethyl acetate as the eluant. The resulting solid obtained was triturated with diethyl ether to provide the desired product.
(2) See Example 1 for reference to starting material.
(3) See Preparation 1 for starting material.
(4) Column chromatography was carried out on silica with a gradient elution using 2:1 ethyl acetate/dichloromethane followed by ethyl acetate as the eluant. The appropriate fractions were combined and evaporated and the material obtained was further purified by column chromatography on silica using 93:7:1 dichloromethane/methanol/0.880 aqueous ammonia as the eluant. The appropriate fractions were combined and evaporated and the residue triturated with diethyl ether to provide the desired product.
(5) The enantiomeric pair obtained was resolved by H.P.L.C. using a similar method to that described in Example 2. This provided the individual enentiomers, one of m.p. 83°–84° C. and $[\alpha]_D^{25}$ −80° (c=1 mg/ml in methanol) and the other m.p. 78°–79° C. and $[\alpha]_D^{25}$ +82° (c=1 mg/ml in methanol).
(6) Column chromatography was carried out on silica using 80:20:1.5 hexane/isopropanol/0.880 aqueous ammonia as the eluant. The appropriate fractions were combined and evaporated and the material obtained was further purified by column chromatography on silica using 97:3 ethyl acetate/ethanol as the eluant. The appropriate fractions were combined and evaporated to provide the separated enantiomeric pairs. Each enantiomeric pair was triturated with diethyl ether to provide the desired product.
(7) The enantiomeric pair obtained was resolved by H.P.L.C. using a similar method to that described in Example 2.

EXAMPLE 7

2-(2,4-Difluorophenyl)-3-(5-fluoropyrimidin-4-yl)-1-(1H-1,2,4triazol-1-yl)butan-2-ol

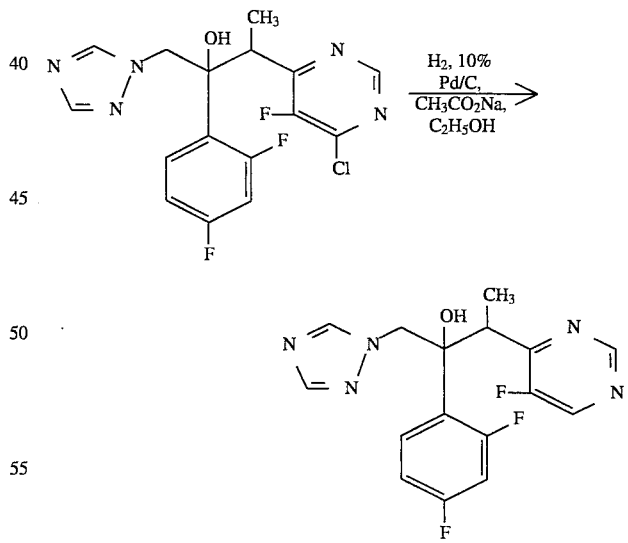

A solution of 3-(4-chloro-5-fluoropyrimidin-6-yl)-2-(2,4-difluorophenyl)-1-(1H-1,2,4-triazol-1-yl)butan-2-ol, enantiomeric pair B (see Preparation 2(iii)) (0.307 g, 0.8 mmol) in ethanol (20 ml) was hydrogenated at atmospheric pressure and at room temperature in the presence of 10% palladium-on-charcoal (30 mg) and sodium acetate (0.082 g, 1 mmol). After 5 hours a further 10 mg of 10% palladium-on-charcoal was added and hydrogenation was continued for an additional 1 hour period. The catalyst was removed by filtration and the filtrate was concentrated in vacuo. "Flash" chromatography of the residue on silica using 97:3 ethyl acetate/ methanol as the eluant provided, after combination and evaporation of appropriate fractions and trituration with diethyl ether, the title compound, enantiomeric pair B, (0.249 g, 89%), m.p. 127° C. Found: C,55.08; H,4.00; N, 19.96; $C_{16}H_{14}F_3N_5O$ requires: C,55.01; H,4.01;N,20.05%.

A sample of the title compound, enantiomeric pair B, (0.105 g, 0.3 mmol) and 1R-(−)-10-camphorsulphonic acid (0.07 g, 0.3 mmol) were dissolved in methanol (4 ml) then cooled to 0° C. for 2 hours. The resulting crystalline solid was collected by filtration to give 2R,3S-2-(2,4difluorophenyl)-3-(5-fluoropyrimidin-4-yl)-1-(1H-1,2,4-triazol-1-yl)butan-2-ol 1R-(−)-10-camphorsulphonate 0.5 methanol (0.06 g), m.p. 176° C., $[\alpha]^{25}_D$ −49.5° (c=2 mg/ml in methanol). Found: C,53.09; H,5.36; N,11.43; $C_{26}H_{30}F_3N_5O_5S.0.5$ $CH_3OH$ requires: C,53.27; H,5.36; N,11.73%. The absolute configuration of the compound was confirmed by single crystal X-ray analysis.

The filtrate from the crystallisation was evaporated in vacuo and partitioned between dichloromethane (10 ml) and saturated aqueous sodium bicarbonate solution (5 ml). The organic layer was dried over magnesium sulphate, filtered and concentrated under reduced pressure. The residue and 1S-(+)-10-camphorsulphonic acid (0.46 g, 0.2 mmol) were dissolved in methanol (3 ml) then cooled to 0° C. for 2 hours. The crystalline solid was collected by filtration to give 2S,3R-2-(2,4-difluorophenyl)-3-(5-fluoropyrimidin-4-yl)-1-(1H-1,2,4-triazol-1-yl)butan-2-ol 1S-(+)-10-camphorsulphonate 0.5 methanol (0.052 g), m.p. 176° C., $[\alpha]_D^{25}$ +54.5° (c=2 mg/ml in methanol). Found: C,53.27; H,5.31; N,11.64; $C_{26}H_{30}F_3N_5O_5S$. 0.5 $CH_3OH$ requires: C,53,27; H,5.36; N,11.73%.

A sample of the 1R-(−)-10-camphorsulphonate salt (1.22 g, 2.1 mmol) prepared according to the above method was partitioned between dichloromethane (20 ml) and saturated aqueous sodium bicarbonate (3 ml). The organic layer was washed with water (5 ml) then dried over magnesium sulphate, filtered and evaporated in vacuo to give 2R,3S-2-(2,4-difluorophenyl)-3-(5-fluoropyrimidin-4-yl)- 1-(1H-1,2, 4-triazol-1-yl)butan-2-ol (0.63 g), m.p. 127° C., $[\alpha]_D^{25}$−62° (c=1 mg/ml in methanol).

A sample of the 1S-(+)-10-camphorsulphonate salt (1.17 g, 2.0 mmol) prepared according to the above method was treated by a similar method to that described above for the 1R-(−)-10-camphorsulphonate salt to give 2D,3R,2-(2,4-difluorophenyl)-3-(5-fluoropyrimidin-4-yl-1-(1H-1,2,4-triazol-1-yl)butan-2-ol (0.63 g), m.p. 127° C., $[\alpha]^{25}_D$ 59.5° (c=2 mg/ml in methanol).

EXAMPLE 8

2-(2,4-Difluorophenyl)-3-(5-fluoropyrimidin-4-yl)-1-(1H-1,2,4-triazol-1-yl)butan-2-ol, enantiomeric pair B

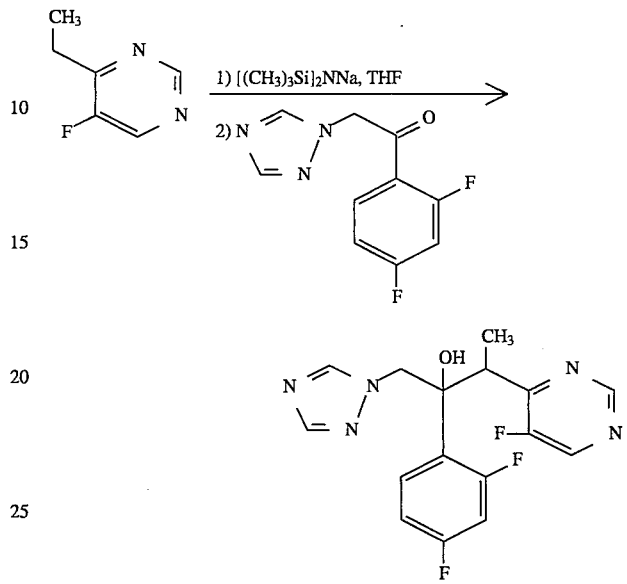

To THF (200 ml) was added sodium bis(trimethylsilyl)amide (79 ml of a 1.0M solution in THF) and the solution cooled to −65° C. under nitrogen. A solution of 4-ethyl-5-fluoropyrimidine (10 g) (see Preparation 8) in THF (100 ml) was added over 30 minutes. After stirring for 3 hours at −65° C. the thin slurry was treated with a solution of 1-(2,4-difluorophenyl)-2-(1H-1,2,4-triazol-1-yl)ethanone (17.7 g) in THF (100 ml), dropwise over 30 minutes. The solution was stirred for a further 1 hour at −65° C. and then treated with acetic acid (20 ml). After warming to −20° C. the solution was washed with water (200 ml) and the organic layer separated and combined with an ethyl acetate (200 ml) back extract of the aqueous phase. The combined organic layers were concentrated under reduced pressure to provide a solid that was triturated with diethyl ether (230 ml) and filtered. The filtrate was concentrated under reduced pressure and chromatographed on silica with 1:1 diethyl ether/ ethyl acetate as the eluent. The fractions containing the title compound were combined, concentrated under reduced pressure and the residue chromatographed on silica with 1:1 ethyl acetate/hexane as the eluent. The appropriate fractions were combined and evaporated under reduced pressure to provide the purified title compound (0.82 g), m.p. 125°–127° C. Found: C,54.89; N,19.66; $C_{16}H_{14}F_3N_5O$ requires: C,55.01; H,4.01; N,20.05%.

EXAMPLE 9

2-(2,4-Difluorophenyl)-3-(5-fluoropyrimidin-4-yl)-1-(1-1,2,4-triazol-1-yl)butan-2-ol, enantiomeric pair A The title compound was prepared by a similar method to that used in Example 7 using 3-(4-chloro-5-fluoropyrimidin-6-yl)-2-(2,4difluorophenyl)- 1-(1H-1,2,4-triazol-1-yl)butan-2ol, enantiomeric pair A (see Preparation 2(iii)) as the starting material. This gave the product, m.p. 137° C. Found:

C,54.89; H,4.06; N,19.82; $C_{16}H_{14}F_3N_5O$ requires: C,55.01; H,4.01; N,20.05%.

EXAMPLE 10

3-(5-Chloropyrimidin-4-yl)-2-(2,4-difluorophenyl)- 1-(1H-1,2,4-triazol- 1-yl)butan-2-ol, enantiomeric pair B

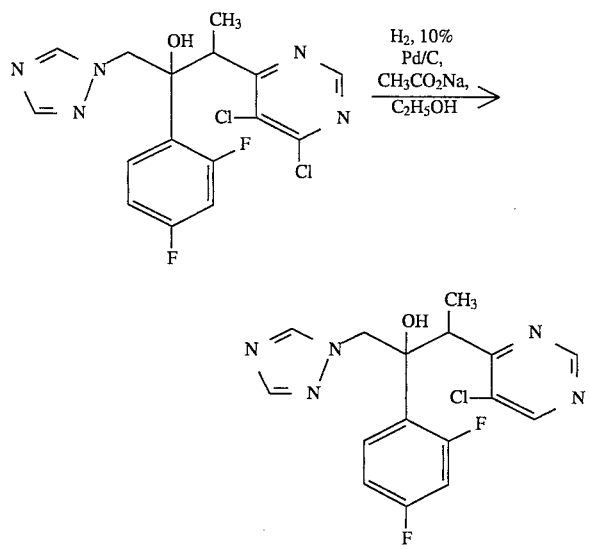

A solution of 3-(4,5-dichloropyrimidin-6-yl)-2-(2,4-difluorophenyl)- 1-(1H-1,2,4-triazol-1-yl)butan-2-ol, enantiomeric pair B (see Preparation 6(iii)) (0.58 g, 1.46 mmol) in ethanol (20 ml) was hydrogenated at atmospheric pressure and at room temperature in the presence of 10% palladium-on-charcoal (45 mg) and sodium acetate (122 mg, 1.5 mmol) for 7 hours. The catalyst was then removed by filtration and the filtrate was concentrated under reduced pressure. "Flash " chromatography of the residue on silica using ethyl acetate as the eluant provided, after combination and evaporation of the appropriate fractions, the title compound (0.35 g, 72%), m.p. 128° C. Found: C,51.68; H,3.89; N,18.58; $C_{16}H_{14}ClF_2N_5O.0.3\ H_2O$ requires: C,51.76; H,3.94; N,18.87%.

EXAMPLE 11

3-(5-Chloropyrimidin-4-yl)-2-(2,4-difluorophenyl)- 1-(1H-1,2,4-triazol- 1-yl)butan-2-ol, enantiomeric pair A The title compound was obtained by a similar method to that used in Example 10 using 3-(4,5-dichloropyrimidin-6-yl)-2-(2,4-difluorophenyl)- 1-(1H-1,2,4-triazol-1-yl)butan-2-ol, enantiomeric pair A (see Preparation 6(iii)) as the starting material. This gave the product as a gum that was characterised by $^1$H-NMR spectroscopy.

$^1$H-NMR (CDCl$_3$) δ=1.50 (d, 3H), 4.4 (q, 1H), 4.67 and 4.82 (AB q, 2H), 6.35 (s, 1H (OH)), 6.45 (m, 1H), 6.62 (m, 1H), 7.07 (m, 1H), 7.6 (s, 1H), 8.05 (s, 1H), 8.5 (s, 1H), 8.8 (s, 1H) ppm.

EXAMPLES 12 to 16

The following tabulated compounds of the general formula:

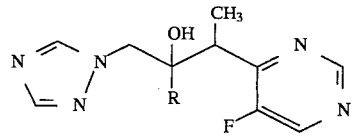

were prepared by a similar method to that described for Example 10 using the appropriate 2-aryl-3-(4-chloro-5-fluoropyrimidin-6-yl)-1-(1H-1,2,4-triazol- 1-yl)butan-2ol as the starting material.

| Example No. | R | Enantiomeric pair | m.p. (°C.) | Analysis |
|---|---|---|---|---|
| 12[(1)] | (3)\~ 2-F-phenyl | B | 94 | Found: C,58.17; H,4.68; N,21.12; $C_{16}H_{15}F_2N_5O$ requires: C,58.01; H,4.53; N,21.15%. |
| 13[(2)] | (3)\~ 2-F-phenyl | A | 117 | Found: C,58.22; H,4.68; N,21.01; $C_{16}H_{15}F_2N_5O$ requires: C,58.01; H,4.53; N,21.15%. |
| 14 | (4)\~ 2-Cl-phenyl | B | 103–104 | Found: C,55.58; H,4.30; N,20.05; $C_{16}H_{15}ClFN_5O$ requires: C,55.26; H,4.35; N,20.14%. |
| 15 | (4)\~ 2-Cl-phenyl | A | 121–122 | Found: C,55.53; H,4.25; N,20.16; $C_{16}H_{15}ClFN_5O$ requires: C,55.26; H,4.35; N,20.14%. |

| Example No. | R | Enantiomeric pair | m.p. (°C.) | Analysis |
|---|---|---|---|---|
| 16[6] | 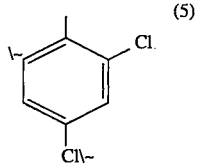 | B | 150–152 | Found: C,50.23; H,3.61; N,18.13; $C_{16}H_{14}Cl_2FN_5O$ requires: C,50.28; H,3.69; N,18.32%. |

(1) Column chromatography was carried out on silica using 96:4 ethyl acetate/methanol as the eluant.
(2) Column chromatography was carried out on silica using isobutylmethylketone as the eluant.
(3) See Preparation 3 for starting material.
(4) See Preparation 4 for starting material.
(5) See Preparation 5 for starting material.
(6) The enantiomeric pair obtained was resolved by H.P.L.C. using a similar method to that described in Example 2.

EXAMPLE 17

An aqueous saline solution of 2R,3S-2-(2,4-difluorophenyl)-3-(5-fluoropyrimidin-4-yl)-1-(1H-1,2,4-triazol-1-yl)butan-2ol and hydroxypropyl-β-cyclodextrin Hydroxypropyl-β-cyclodextrin (Molar Substitution=0.41, 1 g) was placed in a 10 ml volumetric flask and dissolved in distilled water (ca. 7 ml). Sodium chloride (90 mg) was added and dissolved in the solution and the volume made up to 10 ml with distilled water. The resulting solution was added to 2R,3S-2-(2,4-difluorophenyl)-3-(5-fluoropyrimidin- 4-yl)-1-(1H-1,2,4-triazol-1-yl)butan-2ol (100 mg) (see Example 7) in a vial and the mixture was sonicated for 15 minutes and then further mixed by mechanical rotation of the vial for 2 days. A further quantity of hydroxypropyl-β-cyclodextrin (200 mg) was then added and the mixture mixed by mechanical rotation of the vial for 1 hour to provide the title solution.

The following Preparations illustrate the preparation of certain novel starting materials used in the Examples.

Preparation 1

4-Ethyl-3-fluoropyridine

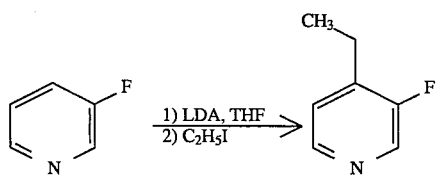

To a stirred solution of LDA (200 mmol) in dry THF (400 ml) (prepared by a similar method to that used in Example 1) at −70° C. and under a nitrogen atmosphere was added dropwise 3-fluoropyridine (20 g, 200 mmol). After 30 minutes at this temperature ethyl iodide (60 g, 370 mmol) was added dropwise to the reaction and the mixture was allowed to warm slowly to between −10° and −5° C. whereupon an exotherm occurred and the temperature rose to 15° to 20° C. The mixture was stirred for a further 30 minutes after which time the reaction was quenched by the addition of water (50 ml) and the organic phase separated. The aqueous phase was extracted with ether (3×50 ml) and the combined organic layers were dried over magnesium sulphate and concentrated under reduced pressure. The resulting liquid was distilled at atmospheric pressure to yield the title compound (13 g), b.p. 154°–158° C., which was characterised by $^1$H-NMR spectroscopy.

$^1$H-NMR (CDCl$_3$): δ=1.25 (t, 3H, J=10 Hz), 2.65 (q, 2H, J=10 Hz), 7.1 (t, 1H, J=8Hz), 8.33 (s, 1H) ppm.

PREPARATION 2

3-(4-Chloro-5-fluoropyrimidin-6-yl)-2-(2,4-difluorophenyl)-1-(1H-1,2,4-triazol-1-yl)butan-2-ol

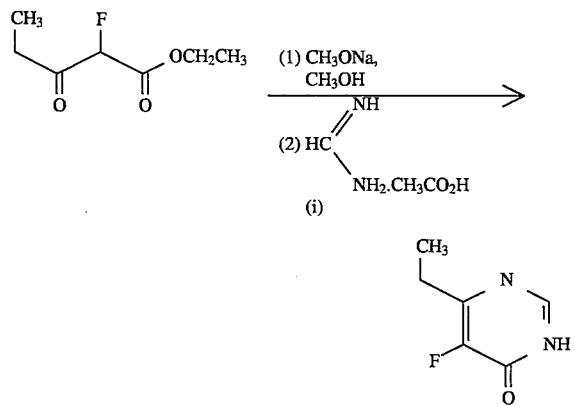

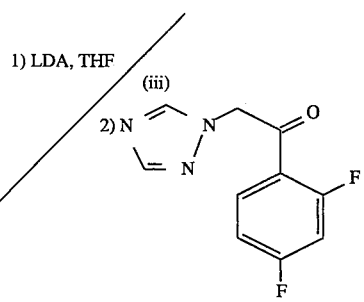

-continued

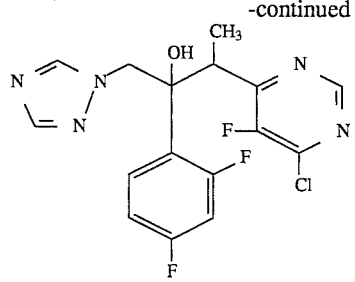

(i) 6-Ethyl-5-fluoropyrimidin-4(3H)-one

To a solution of sodium methoxide (8.64 g, 160 mmol) in methanol (50 ml) at 0° C. was added a solution of ethyl α-fluoropropionylacetate (see E. D. Bergmann et al, J. Chem. Soc., 1959, 3278 and D. J. Burton et al, Tet. Lett., 30, 6113 (1989)) (12.96 g, 80 mmol) and formamidine acetate (8.32 g, 80 mmol) in methanol (50 ml) and the resulting mixture was stirred at 0° C. for 1 hour, overnight at room temperature and finally for 30 minutes under reflux. The mixture was cooled and the excess sodium methoxide was nuetralised by the addition of glacial acetic acid (10 g). The reaction was concentrated under reduced pressure and the residue was dissolved in hot ethyl acetate, the insoluble sodium acetate was removed by filtration and the filtrate was concentrated under reduced pressure. "Flash" chromatography of the residue using ethyl acetate as the eluant provided, after combination and evaporation of appropriate fractions and trituration with diethyl ether, the title compound (5.5 g, 48%), m.p. 105°–106° C. Found: C,50.38; H,4.85; N,19.63; $C_6H_7FN_2O$ requires: C,50.70; H,4.93; N,19.72%.

The title compound may also be prepared as described in Preparation 7.

(ii) 4-Chloro-6-ethyl-5-fluoropyrimidine

A mixture of the product of part (i) (6.4 g, 45 mmol) and phosphoryl chloride (30 ml) was heated under reflux for 3 hours. The excess phosphoryl chloride was removed by distillation under reduced pressure and the residue was poured into ice-water. The resulting mixture was extracted with methylene chloride (3×50 ml) and the combined organic extracts were washed with water and dried over magnesium sulphate. The solvent was removed under reduced pressure and the resulting oil was distilled under reduced pressure to provide the title compound (4.81 g, 66%), b.p. 74° C. at 22 mm Hg, which was characterised by $^1$H-NMR spectroscopy.

$^1$H-NMR (CDCl$_3$): δ=1.3 (t, 3H, J=10 Hz), 2.9 (q, 2H, J=10 Hz), 8.68 (s, 1H) ppm.

(iii) 3-(4-Chloro-5-fluoropyrimidin-6-yl)-2-(2,4-difluorophenyl)- 1-(1H-1,2,4-triazol-1-yl)butan-2-ol To a solution of LDA (20 mmol) in THF$^1$ (50 ml) (prepared by a similar method to that used in Example 1) under a nitrogen atmosphere and at −70° C. was added dropwise a solution of the product of part (ii) (3.2 g, 20 mmol) in THF$^1$ (30 ml) over 15 minutes. The resulting mixture was stirred at this temperature for 3 hours. To the resulting solution was added a solution of 1-(2,4-difluorophenyl)-2-( 1H-1,2,4-triazol-1-yl)ethanone (4.46 g, 20 mmol) in THF (50 ml) and the mixture was maintained at −70° C. for 1 hour and then at −50° C. for a further 1 hour. The reaction was quenched by the addition of a solution of glacial acetic acid (1.2 g) in water (10 ml) and the mixture was allowed to warm to room temperature. The organic phase was separated, the aqueous phase extracted with ethyl acetate (20 ml) and the combined organic layers were dried over magnesium sulphate and concentrated under reduced pressure. Column chromatography of the residue on silica using 3:2 ethyl acetate/diethyl ether as the eluant first gave, after combination and evaporation of appropriate fractions and trituration with diethyl ether, the title compound, enantiomeric pair B (0.94 g, 12%), m.p. 92° C. Found: C,49.93; H,3.57; N,18.17; $C_{16}H_{13}ClF_3N_5O$ requires: C50.06; H,3.39; N,18.25%.

Further elution gave, after combination and evaporation of appropriate fractions, the title compound, enantiomeric pair A contaminated with ketone starting material. This was purified by several recrystallisations from diethyl ether to provide the product, m.p. 132° C. Found: C,49.93; H,3.58; N,18.23; $C_{16}H_{13}ClF_3N_5O$ requires: C,50.06; H,3.39; N,18.25%.

(1) THF may be replaced by toluene.

Preparations 3 to 5

The following tabulated compounds of the general formula:

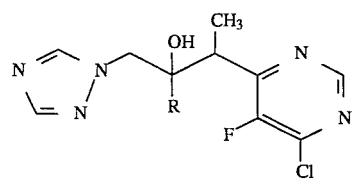

were prepared by a similar method to that described in Preparation 2(iii) using 4-chloro-6-ethyl-5-fluoropyrimidine and the appropriate 1-aryl-2-(1H-1,2,4-triazol-1-yl) ethanone as the starting materials.

| Preparation | R | Enantiomeric pair | m.p. (°C.) | Analysis |
|---|---|---|---|---|
| 3 | (2-F-phenyl) | B | 95 | Found: C,52.22; H,3.92; N,19.08; $C_{16}H_{14}ClF_2N_5O$ requires: C,52.53; H,3.83; N,19.15%. |
|   |   | A | 110 | Found: C,53.17; H,4.00; N,19.27; $C_{16}H_{14}ClF_2N_5O$ requires: C,52.53; H,3.83; N,19.15%. |
| 4 | (2-Cl-phenyl) | B | 118–119 | Found: C,50.65; H,3.71; N,18.12; $C_{16}H_{14}Cl_2FN_5O$ requires: C,50.28; H,3.69; N,18.32%. |
|   |   | A | 119–120 | Found:C,50.54 H,3.71 N,18.16; $C_{16}H_{14}Cl_2FN_5O$ requires: C,50.28; H,3.69; N,18.32%. |

| Preparation | R | Enantiomeric pair | m.p. (°C.) | Analysis |
|---|---|---|---|---|
| 5 | 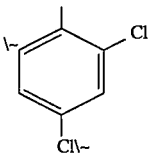 | B | 123–124 | Found: C,46.49; H,3.05; N,16.69; $C_{16}H_{13}Cl_3FN_5O$ requires: C,46.12; H,3.05; N,16.81%. |

Preparation 6

3-(4,5-Dichloropyrimidin-6-yl)-2-(2,4-difluorophenyl)-1-(1H- 1,2,4triazol-1-yl)butan-2-ol

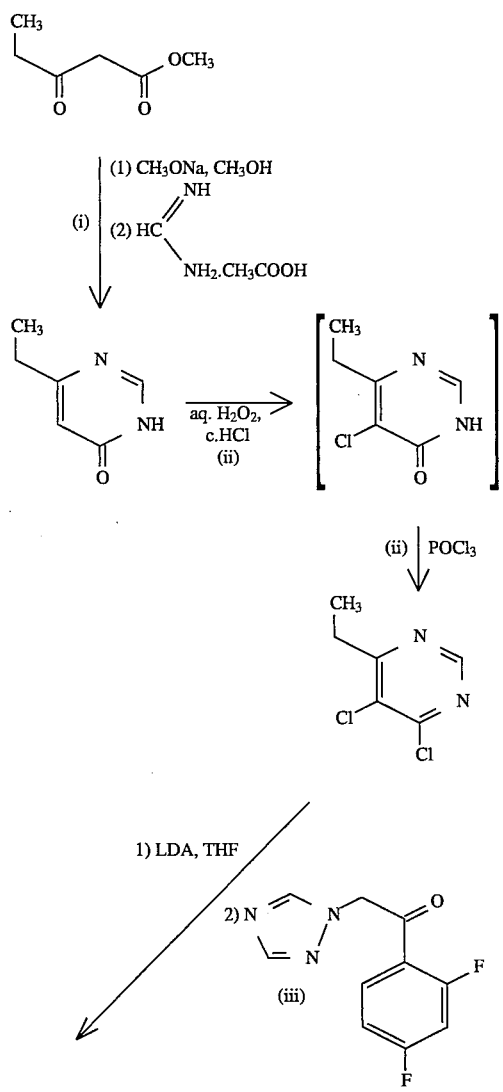

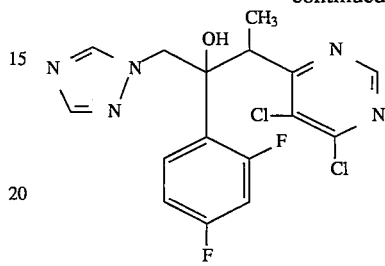

(i) 6-Ethylpyrimidin-4 (3H)-one

To a solution of sodium methoxide (4.19 kg, 77.6 mol) and formamidine acetate (3.0 kg, 28.8 mol) in methanol (45 L) at 5°–10° C. was added slowly a solution of methyl propionylacetate (2.5 kg, 19.2 mol) in methanol (10 L) maintaining the temperature below 20° C. throughout the addition. The resulting mixture was stirred at room temperature overnight after which time the pH was adjusted to 7 by the addition of concentrated under reduced pressure to reaction mixture was concentrated under reduced pressure to ca.10 L in volume, diluted with water (10 L) and was extracted with 2-butanone (2×30 L). The combined organic extracts were concentrated under reduced pressure to ca. 2 L in volume and diluted with ethyl acetate (4 L). The desired product crystallised from the solution (2.4 kg, 70%) and was rectystallised from isopropanol to yield a product of m.p. 132°–134° C. Found: C,58.45; H6.37; N,22.41; $C_6H_8N_2O$ requires: C,58.05; H,6.50; N,22.57%.

(ii) 4,5-Dichloro-6-ethylpyrimidine

To a solution of 6-ethylpyrimidin-4(3H)-one (the product of part (i)) (18.6 g, 150 mmol) in concentrated hydrochloric acid (120 ml) at 30°–40° C. was added dropwise a 30 wt. % solution of hydrogen peroxide in water (18 ml) over a period of 30 minutes (slight exotherm resulted) and the resulting mixture was stirred overnight at 40° C. The mixture was concentrated under reduced pressure and the residue was suspended/dissolved in toluene and the toluene residue under reduced pressure.

The residue was dissolved in chloride (150 ml) and heated under reflux for 3 hours after which time the excess phosphorus oxychloride was removed under reduced pressure. The residue was poured into ice/water, extracted with methylene chloride (3×50 ml) and the combined organic extracts were washed with water (30 ml) and dried over magnesium sulphate. The solvent was removed under reduced pressure and the resulting oil was distilled under reduced pressure to yield the title compound (5.4 g, 20%), b.p. 104° C. at 22 mm Hg, which was characterised by $^1$H-NMR spectroscopy.

$^1$H-NMR (CDCl$_3$): δ=1.3 (t, 3H, J=10 Hz), 3.04 (q, 2H, J=10 Hz) 8.75 (s 1H) ppm.

(iii) 3-(4,5-Dichloropyrimidin-6-yl)-2-(2,4-difluorophenyl)-1-(1H-1,2,4-triazol-1-yl)butan-2-ol To a solution of LDA (13.6 mmol) in THF (50 ml) (prepared by a similar method to that used in Example 1) at −70° C. was added dropwise 4,5-dichloro-6-ethylpyrimidine (the product of part (ii)) (2.37 g, 13.3 mmol) and the resulting solution was stirred at this temperature for 10 minutes. A solution of 1-(2,4-difluorophenyl)-2-(1H-1,2,4-triazol-1-yl)ethanone (2.97 g 13.3 mmol) in THF (50 ml) was added to the reaction mixture at such a rate so as to maintain the reaction temperature below −50° C. After stirring at −70° C. for 1 hour and at −50° C. for a further 1 hour the reaction was quenched by the addition of 10% aqueous acetic acid (11 ml).

The organic was separated, the aqueous phase extracted with ethyl acetate (2×20 ml) and the combined organic layers were dried over magnesium sulphate. After removal of the solvent under reduced pressure, the residue was triturated with diethyl ether (25 ml) and the unreacted ketone starting material (1.7 g) was removed by filtration. The filtrate was concentrated under reduced pressure and "flash" chromatography of the residue on silica using 65:35 ethyl acetate/diethyl ether as the eluant first provided, after combination and evaporation of appropriate fractions and trituration with diethyl ether, the title compound, enantiomeric pair B as a solid (607 mg, 13%), m.p. 124° C. Found: C,47.78; N,3.33; N,17.13; $C_{16}H_{13}Cl_2F_2N_5O$ requires: C,48.00; H,3.25; N,17.50%.

Further elution gave, after combination and evaporation of appropriate fractions ad trituration with diethyl ether, the title compound, enantiomeric pair A as a solid (527 mg, 10%), m.p. 137° C. Found: C,48.02; H,3.30; N,17.39; $C_{16}H_{13}Cl_2F_2N_5O$ requires: C,48.00; H,3.25; N,17.50%.

Preparation 7

6-Ethyl-5-fluoropyrimidin-4(3H)-one

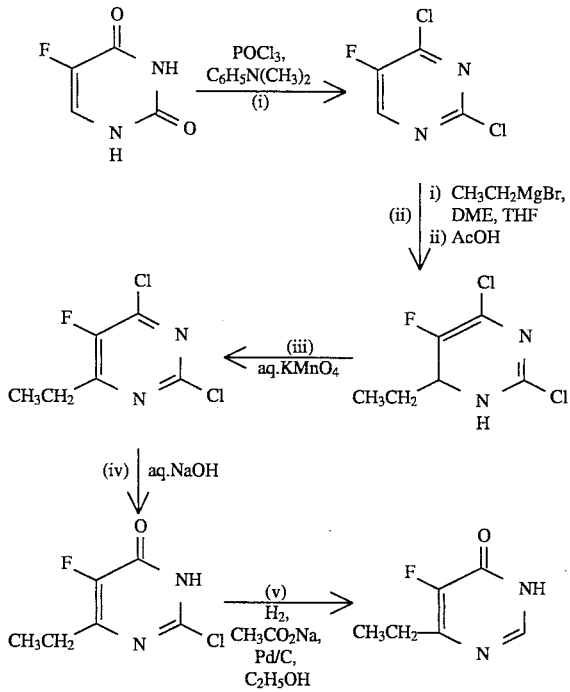

(1) 2,4-Dichloro-5-fluoropyrimidine

To phosphorus oxychloride (141.4 g) at 25° C. was added powdered 5-fluorouracil (20 g). The resulting slurry was heated to 90° C. and N,N-dimethylaniline (37.3 g) was added over 1 hour. The reaction was then heated at reflux for 5 hours and 70 g of the phosphorus oxychloride was removed by distillation. The mixture was then cooled to 25° C. and quenched into 3N HCl (200 ml) at 0° C., portionwise over 1 hour. The title compound was then extracted from the mixture using dichloromethane (2×70 ml). The combined dichloromethane layers were washed with water (50 ml) and concentrated under vacuum to give an oil (24 g), which was characterised by $^1$H-NMR and mass spectrometry.

$^1$H-NMR (CDCl$_3$): δ=8.5 (s, 1H) ppm.

Mass Spec.: m/e=166.

(ii) 2,4-Dichloro-1,6-dihydro-6-ethyl-5-fluoropyrimidine

To magnesium turnings (4.27 g) in tetrahydrofuran (56 ml) was added a solution of bromoethane (19 g) in THF (19 ml) over 5 hours. To this slurry at 0° C. was added a solution of the product of part (i) (24 g) in 1,2-dimethoxyethane (70 ml) over 1 hour. The reaction was quenched at 10° C. using glacial acetic acid (10 g) to give a solution of the title compound which was used directly in the next step.

(iii) 2,4-Dichloro-6-ethyl-5-fluoropyrimidine

To the solution obtained as the product of part (ii) was added a solution of potassium permanganate (23 g) in water (260 ml) over 2 hours, keeping the temperature of the reaction below 20° C. 5N hydrochloric acid (30 ml) was then added followed by a solution of sodium metabisulphite (14 g) in water (42 ml). After decolourisation of the mixture the product was extracted into ethyl acetate (250 ml). The organic layer was then concentrated to give an oil. The oil was partitioned between dichloromethane (50 ml) and 2N sodium hydroxide (105 ml) and the organic layer was washed with 5% brine (100 ml). The organic layer was concentrated to give a solution of the title compound which was used directly in the next step.

(iv) 2-Chloro-6-ethyl-5-fluoropyrimidin-4(3H)-one

To the solution obtained as the product of part (iii) was added water (6 ml). The mixture was stirred at 80° C. and 4N sodium hydroxide (45 ml) was added slowly over 2 hours. At the end of this period the reaction was cooled and washed with dichloromethane (15 ml). The aqueous layer was then added to dichloromethane (60 ml) and the pH adjusted to 1 with concentrated hydrochloric acid. The organic layer was separated and the pH adjusted to 3 using concentrated aqueous ammonia solution. The precipitate of ammonium chloride was removed by filtration and the filtrate was then concentrated to a volume of 15 ml and diluted with ethyl acetate (150 ml). This solution was concentrated to a volume of 30 ml and the crystals of the title compound that formed were collected by filtration and dried (8 g), then characterised by $^1$H-NMR and mass spectrometry.

$^1$H-NMR (dmso-d$_6$): δ=7.3 (exchangeable), 2.4 (m, 2H), 1.1 (t, 3H) ppm.

Mass Spec.: m/e=176.

(v) 6-Ethyl-fluoropyrimidin-4(3H)-one

To the product of part (iv) (6 g) in ethanol (60 ml) was added sodium acetate (5.5 g) and 5% palladium-on-carbon (0.6 g). The mixture was hydrogenated at 3 atmospheres pressure for 8 hours. The catalyst was removed by filtration and the filtrate was concentrated to a volume of 10 ml then mixed with water (2 ml) and dichloromethane (80 ml). Toluene (32 ml) was added and the solution was concentrated to a volume of 5–6 ml and then mixed with further toluene (8 ml). The crystals of the title compound that separated were isolated by filtration and characterised by $^1$H-NMR and mass spectrometry (Yield=3.9 g).

$^1$H-NMR (dmso-d$_6$): δ=8.0 (s, 1H), 2.5 (m, 2H), 1.15 (t, 3H) ppm.

Mass spec.: m/e=142.

Preparation 8

4-Ethyl-5-fluoropyrimidine

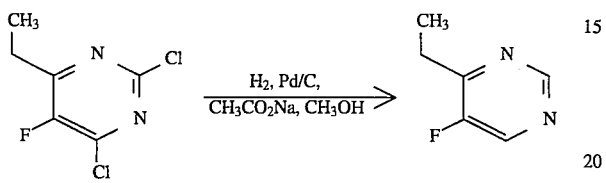

A mixture of 2,4-dichloro-6-ethyl-5-fluoropyrimidine (10 g) (see Preparation 7(iii)), sodium acetate (8.83 g), 5% palladium-on-charcoal (50% "wet", 2 g) and methanol (30 ml) was hydrogenated at 50° C. and 3 atmospheres pressure for 5 hours. The resulting slurry was filtered carefully through a cellulose-based filter-aid, the pad was washed with further methanol (5 ml) and the resulting orange filtrate was distilled at 64° C. and atmospheric pressure to provide a colourless distillate. This was partitioned between water (300 ml) and ether (40 ml) and the two phases separated. The organic phase was with water (4×50 ml), dried over MgSO$_4$ and the solvent was removed at room temperature under reduced pressure to provide the title compound as a pale yellow liquid (2.2 g).

Preparation 9

2-Chloro-4-ethyl-5-fluoropyrimidine

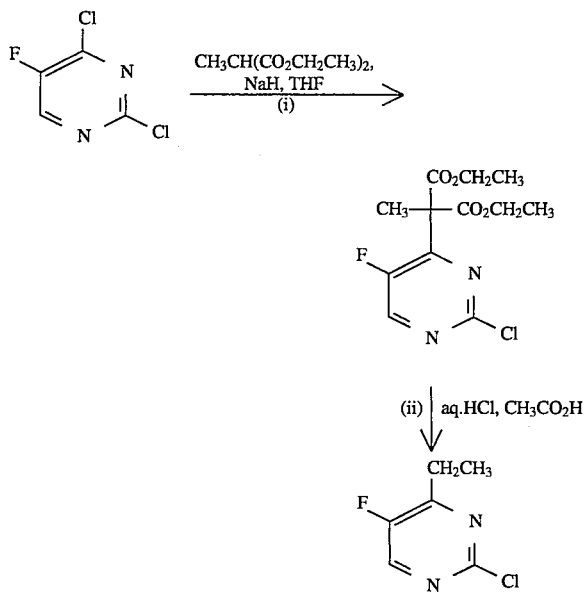

(i) 2-Methyl-2-(2-chloro-5-fluoropyrimidin-4-yl)-1,3-propanedioc acid, diethyl ester Sodium hydride (60% oil dispersion, 2.8 g) and diethyl methylmalonate (6 q) were reacted at −10° C. in THF (200 ml). After 30 minutes a solution of 2,4-dichloro-5-fluoropyrimidine (5 g) (see Preparation 7) in THF (25 ml) was added over 30 minutes at −10° C. The reaction was partitioned between dichloromethane (200 ml) and water (200 ml), acidified with acetic acid and the layers separated. The organic layer was concentrated under reduced pressure to an oil and chromatographed on silica gel using dichloromethane as the eluent. This gave, after the combination and evaporation of appropriate fractions, the title compound (9 g) which was characterised using $^1$H-NMR and mass spectrometry.

$^1$H-NMR (CDCl$_3$): δ=8.5 (d, 1H), 4.6 (m, 4H), 1.9 (s, 3H), 1.3 (t, 3H) ppm.

Mass spec.: m/e=304.

(ii) 2-Chloro-4-ethyl-5-fluoropyrimidine

The product of part (i) (3.2 g) was dissolved in acetic acid (25 ml) and diluted with 5N HCl (10 ml). After heating the mixture at 100° C. for 16 hours the mixture was cooled and partitioned between water (30 ml) and dichloromethane (45 ml). The dichloromethane layer was separated, dried and concentrated under reduced pressure to give an oil. The title compound was isolated by chromatography on silica gel using dichloromethane as the eluent. The product was characterised by $^1$H-NMR and mass spectrometry (yield=350 mg).

$^1$H-NMR (CDCl$_3$): δ=8.4 (s, 1H), 2.9 (m, 2H), 1.3 (t, 3H) ppm.

Mass spec.: m/e=160.

Assessment of in vivo activity against *Aspergillus fumigatus* in mice

Using the general test procedure outlined on page 17 of the description, a group of mice was inoculated with a strain of *Aspergillus fumigatus*. Each mouse was then treated with the test compound at a standard dose of 20 mg/kg b.i.d. for 5 days. The mice were then assessed on the tenth day.

Activity is bas on the survival of a treated group of mice after the death of an untreated of mice, and also on the number of mice cured of the infection.

The results obtained in a comparative study using two compounds described in the specific Example of the present application and two compounds described in the specific Example of European Patent Application No. 89307920.2 (EP-A-0357241) are shown in the following table:

| Reference to test compound | Structure | Survivors (expressed as number from a test group of five mice) | Cured[1] (expressed as number from a test group of five mice) |
| --- | --- | --- | --- |
| Example 2, enantiomeric pair B | 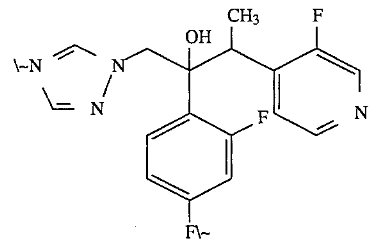 | 5/5 | 5/5 |
| Example 2, "diastereomeric pair B" from EP Application No. 89307920.2 | 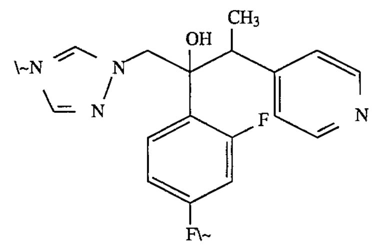 | 4/5 | 0/5[2] |
| Example 7, enantiomeric pair B | 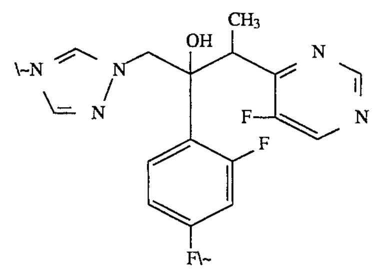 | 5/5 | 4/5 |
| Example 3, "diastereomeric pair B" from EP Application No. 89307920.2 | 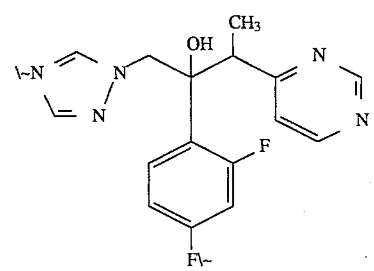 | 3/5 | 0/5[2] |

[1]"Cured" is defined as completely free of infection on the tenth day.
[2]Although in these cases the mice were not "cured" as defined above, progression of the infection was significantly reduced.

We claim:

1. A compound of the formula

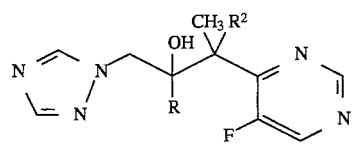

or a pharmaceutically acceptable salt thereof, wherein R is 2,4-difluorophenyl, and $R^2$ is hydrogen or methyl.

2. A compound of the formula

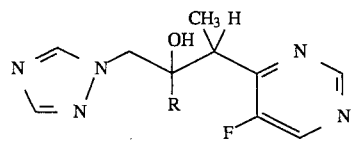

or a pharmaceutically acceptable salt thereof, wherein R is 2,4-difluorophenyl, 2,4-dichlorophenyl, 2-chlorophenyl, 4-fluorophenyl, or 2-fluorophenyl.

3. 2-(2,4-difluorophenyl)-3-(5-fluoropyrimidin-4-yl)-1-(1H-1,2,4-triazol-1-yl)butan-2-ol, or a pharmaceutically acceptable salt thereof.

4. (2R,3S)-2-(2,4-difluorophenyl)-3-(5-fluoropyrimidin-4-yl)-1-(1H-1,2,4-triazol-1-yl)butan-2-ol, or a pharmaceutically acceptable salt thereof.

5. A pharmaceutical composition for treating a fungal infection in a mammal which comprise an effective amount of the compound of claim 1 and a pharmaceutically acceptable carrier.

6. A pharmaceutical composition for treating a fungal infection in a mammal which comprises an effective amount of the compound of claim and a pharmaceutically acceptable carrier.

7. A pharmaceutical composition for treating a fungal infection in a mammal which comprises an effective amount of the compound of claim 3 and a pharmaceutically acceptable carrier.

8. A pharmaceutical composition for treating a fungal infection in a mammal which comprises an effective amount of the compound of claim 4 and a pharmaceutically acceptable carrier.

9. A method of treating a fungal infection in a mammal which comprises administering to said mammal an effective amount of the compound of claim 1.

10. A method of treating a fungal infection in a mammal which comprises administering to said mammal an effective amount of the compound of claim 2.

11. A method of treating a fungal infection in a mammal which comprise administering to said mammal an effective amount of the compound of claim 3.

12. A method of treating a fungal infection in a mammal which comprised administering to said mammal an effective amount of the compound of claim 4.

* * * * *

UNITED STATES PATENT AND TRADEMARK OFFICE
CERTIFICATE OF CORRECTION

PATENT NO. : 5,567,817
DATED : October 22, 1996
INVENTOR(S) : Stephen J. Ray and Kenneth Richardson It is certified that error appears in the above-identified patent and that said Letters Patent is hereby corrected as shown below:

Column 31,
Line 5, insert the claim reference numeral -- 2 -- between the words "claim" and "and" in dependent claim 6.

Signed and Sealed this

Twenty-fourth Day of September, 2002

Attest:

Attesting Officer

JAMES E. ROGAN
Director of the United States Patent and Trademark Office